United States Patent
Vigliotti et al.

(10) Patent No.: US 11,013,610 B2
(45) Date of Patent: May 25, 2021

(54) EXPANDABLE ANTERIOR LUMBAR INTERBODY FUSION DEVICE

(71) Applicant: SPINE WAVE, INC., Shelton, CT (US)

(72) Inventors: Daniel Vigliotti, Guilford, CT (US); Scott McLean, Sandy Hook, CT (US)

(73) Assignee: SPINE WAVE, INC., Shelton, CT (US)

( * ) Notice: Subject to any disclaimer, the term of this patent is extended or adjusted under 35 U.S.C. 154(b) by 301 days.

(21) Appl. No.: 16/157,318

(22) Filed: Oct. 11, 2018

(65) Prior Publication Data

US 2019/0110902 A1   Apr. 18, 2019

Related U.S. Application Data

(60) Provisional application No. 62/573,824, filed on Oct. 18, 2017.

(51) Int. Cl.
*A61F 2/44* (2006.01)
*A61F 2/30* (2006.01)
*A61F 2/46* (2006.01)

(52) U.S. Cl.
CPC ........ *A61F 2/4455* (2013.01); *A61F 2/30771* (2013.01); *A61F 2/447* (2013.01); *A61F 2/4611* (2013.01); *A61F 2002/3055* (2013.01); *A61F 2002/30154* (2013.01); *A61F 2002/30556* (2013.01); *A61F 2002/30593* (2013.01);
(Continued)

(58) Field of Classification Search
CPC .......... A61F 2/44; A61F 2/4455; A61F 2/446; A61F 2/4465; A61F 2/447; A61F 2/4611; A61F 2002/30154; A61F 2002/30556; A61F 2002/30593; A61F 2002/30601; A61F 2002/30622; A61F 2002/30771; A61F 2002/30841; A61F 2002/30843; A61F 2002/30845
See application file for complete search history.

(56) References Cited

U.S. PATENT DOCUMENTS

| | | |
|---|---|---|
| 4,863,476 A | 9/1989 | Shepperd |
| 5,571,109 A | 11/1996 | Bertagnoli |
| 5,980,522 A | 11/1999 | Koros et al. |

(Continued)

OTHER PUBLICATIONS

Written Opinion for PCT/US18/55359, dated Feb. 8, 2019.
International Search Report for PCT/US18/55359, dated Feb. 8, 2019.

*Primary Examiner* — Eric S Gibson
(74) *Attorney, Agent, or Firm* — Hoffmann & Baron, LLP (57) ABSTRACT

An expandable anterior lumbar interbody fusion device comprises a multiple piece construction that includes an outer shell, movable upper and lower endplates and a pair of laterally spaced supports therebetween. The endplates are initially nested within the outer shell and telescope through the outer shell when expanded by a secondary instrument. Each endplate includes fixation elements to anchor the expanded device in an intervertebral disc space. Bilateral internal pockets are formed within each of the endplates to fully contain the supports. Once the device is expanded, the supports are pushed into place by the instrument in a manner to maintain the expanded position. After the supports are in place, the expander instrument is removed, and the device remains anchored in the expanded state.

30 Claims, 7 Drawing Sheets

(52) U.S. Cl.
CPC ............... *A61F 2002/30601* (2013.01); *A61F 2002/30622* (2013.01); *A61F 2002/30845* (2013.01)

(56) References Cited

U.S. PATENT DOCUMENTS

| | | | |
|---|---|---|---|
| 6,045,579 A | 4/2000 | Hochshuler et al. | |
| 6,102,950 A | 8/2000 | Vaccaro | |
| 6,176,882 B1* | 1/2001 | Biedermann | A61F 2/447 623/17.15 |
| 6,419,705 B1 | 7/2002 | Erickson | |
| 6,648,917 B2 | 11/2003 | Gerbec et al. | |
| 6,773,460 B2 | 8/2004 | Jackson | |
| 8,187,332 B2* | 5/2012 | McLuen | A61F 2/446 623/17.16 |
| 8,366,777 B2* | 2/2013 | Matthis | A61F 2/4425 623/17.16 |
| 8,518,120 B2* | 8/2013 | Glerum | A61F 2/447 623/17.16 |
| 9,101,489 B2 | 8/2015 | Protopsaltis et al. | |
| 9,233,007 B2* | 1/2016 | Sungarian | A61F 2/442 |
| 9,492,288 B2* | 11/2016 | Wagner | A61F 2/4611 |
| 9,498,347 B2 | 11/2016 | McLean | |
| 9,788,971 B1* | 10/2017 | Stein | A61F 2/447 |
| 9,801,734 B1* | 10/2017 | Stein | A61F 2/447 |
| 9,987,143 B2* | 6/2018 | Robinson | A61F 2/447 |
| 10,098,758 B2* | 10/2018 | Matthews | A61F 2/447 |
| 10,219,913 B2* | 3/2019 | Matthews | A61F 2/4425 |
| 10,420,654 B2* | 9/2019 | Logan | A61F 2/4465 |
| 10,470,894 B2* | 11/2019 | Foley | A61F 2/4465 |
| 2004/0054412 A1 | 3/2004 | Gerbec et al. | |
| 2006/0122701 A1* | 6/2006 | Kiester | A61F 2/447 623/17.11 |
| 2008/0147193 A1* | 6/2008 | Matthis | A61F 2/4425 623/17.16 |
| 2011/0319997 A1* | 12/2011 | Glerum | A61F 2/442 623/17.15 |
| 2012/0035729 A1* | 2/2012 | Glerum | A61F 2/4611 623/17.15 |
| 2013/0158667 A1 | 6/2013 | Tabor et al. | |
| 2013/0158669 A1* | 6/2013 | Sungarian | A61F 2/447 623/17.16 |
| 2013/0204371 A1* | 8/2013 | McLuen | A61F 2/442 623/17.16 |
| 2013/0274883 A1* | 10/2013 | McLuen | A61F 2/447 623/17.16 |
| 2014/0180421 A1* | 6/2014 | Glerum | A61F 2/4611 623/17.16 |
| 2014/0236296 A1* | 8/2014 | Wagner | A61F 2/447 623/17.15 |
| 2014/0277474 A1* | 9/2014 | Robinson | A61F 2/30744 623/17.15 |
| 2015/0012097 A1* | 1/2015 | Ibarra | A61F 2/442 623/17.15 |
| 2015/0073553 A1* | 3/2015 | Barreiro | A61F 2/4611 623/17.15 |
| 2015/0112438 A1* | 4/2015 | McLean | A61F 2/4455 623/17.16 |
| 2015/0272748 A1* | 10/2015 | McLean | A61F 2/447 623/17.16 |
| 2015/0366675 A1* | 12/2015 | Matthews | A61F 2/30771 623/17.16 |
| 2015/0374509 A1* | 12/2015 | Mclean | A61F 2/4455 623/17.16 |
| 2016/0045328 A1* | 2/2016 | Matthews | A61F 2/30771 623/17.16 |
| 2016/0324661 A1* | 11/2016 | Miller | A61F 2/4425 |
| 2017/0119542 A1* | 5/2017 | Logan | A61F 2/442 |
| 2017/0128226 A1* | 5/2017 | Faulhaber | A61F 2/30767 |
| 2017/0281358 A1* | 10/2017 | Wagner | A61F 2/4455 |
| 2018/0256356 A1 | 9/2018 | Robinson et al. | |
| 2018/0289505 A1* | 10/2018 | Foley | A61F 2/4465 |
| 2019/0110902 A1* | 4/2019 | Vigliotti | A61F 2/30771 |
| 2019/0133780 A1* | 5/2019 | Matthews | A61F 2/4455 |
| 2019/0321190 A1* | 10/2019 | Wagner | A61F 2/4611 |
| 2020/0129307 A1* | 4/2020 | Hunziker | A61F 2/447 |

* cited by examiner

EXPANDABLE ANTERIOR LUMBAR INTERBODY FUSION DEVICE

CROSS-REFERENCE TO RELATED APPLICATION

This application claims priority to U.S. Provisional Patent Application No. 62/573,824, filed Oct. 18, 2017, the entire contents of which are incorporated by reference herein.

FIELD OF THE INVENTION

The subject invention relates generally to the field of spinal implants and more particularly to an expandable anterior lumbar interbody fusion device.

BACKGROUND OF THE INVENTION

Spinal implants such as spinal interbody fusion devices are used to treat degenerative disc disease and other damages or defects in the spinal disc between adjacent vertebrae. The disc may be herniated or suffering from a variety of degenerative conditions, such that the anatomical function of the spinal disc is disrupted. Most prevalent surgical treatment for these conditions is to fuse the two vertebrae surrounding the affected disc. In most cases, the entire disc will be removed, except for a portion of the annulus, by way of a discectomy procedure. A spinal fusion device is then introduced into the intradiscal space and suitable bone graft or bone substitute material is placed substantially in and/or adjacent the device in order to promote fusion between two adjacent vertebrae.

There are various approaches that a surgeon may take to perform spinal fusion. Such approaches include a posterior approach, which is accessed from the back of the spine, or an anterior approach, which is accessed from the front. Other approaches which may be used include a transforaminal approach and a lateral approach, which is accessed from the side of the patient. The particular approach selected is primarily determined by the type of treatment to be administered by the surgeon. For patients that require treatment for conditions including degenerative disc disease, spinal instability or deformity, anterior lumbar interbody fusion (ALIF) has been found to be effective. The ALIF procedure and associated devices have certain advantages over other procedures. The first is that there is typically less disruption to surrounding musculature and nerves. Once access is achieved, there is a relatively open space to work in. This allows for more efficient removal of disc material thereby providing a larger potential fusion bed. The ALIF procedure also allows for a larger implant both in footprint and height, which creates better height and lordosis restoration as well as greater spinal stability.

Anterior lumbar interbody fusion requires an incision through the patient's abdomen and retraction of the surrounding muscles and abdominal contents to the side. After the affected disc is removed a structural ALIF device or implant is inserted which may be packed before, during or after insertion with a suitable bone graft material. Some types of ALIF devices are expandable so as to correct height between adjacent vertebrae. In certain of these expandable ALIF devices only the anterior end is specifically expandable, so as to produce an expansion of the disc height at the anterior side greater than the posterior side in an effort to correct lordosis. Examples of such expandable devices include U.S. Pat. No. 6,773,460, issued to Roger P. Jackson on Aug. 10, 2004, and U.S. Pat. No. 6,102,950, issued to Alex Vacarro on Aug. 15, 2000. While it is typically not desirable to increase the posterior side greater than the anterior side, it is often desirable to increase both the posterior and anterior sides an amount sufficient to not only correct disc height but to also adequately decompress neural elements.

Certain of the known expandable ALIF devices include expansion structure or mechanisms that tend to impede the graft loading process, particularly after expansion. As such, it is desirable that an expandable ALIF device allow for maximum introduction of biologic bone graft material as well as for optimized openings in the inferior and superior surfaces of the ALIF device so as to maximize contact area between graft material and the endplates of the opposing vertebral bodies. One expandable ALIF device that addresses these concerns is shown and described in U.S. Pat. No. 9,101,489, issued to Protopsaltis et al. on Aug. 11, 2015, entitled "Expandable Anterior Lumbar Interbody Fusion Device", and assigned to the same assignee as the present invention. The expandable ALIF device disclosed in the '489 patent comprises a deformable monolithic body having expandable posterior and anterior ends.

Nevertheless, there is still a need for an enhanced expandable ALIF fusion device to further support the needs of the surgeon and to provide improved treatment for the patient.

SUMMARY OF THE INVENTION

It is an object of the invention to provide an improved expandable anterior lumbar interbody fusion device. In accordance with a particular aspect, the expandable anterior lumbar interbody fusion device a comprises a multiple piece construction that includes an outer shell, upper and lower movable endplates and support members. The endplates are initially nested within the outer shell and telescope through the outer shell when expanded by a secondary instrument. Once expanded, the supports are pushed into place by the instrument to maintain the expanded height of the device. Bilateral internal pockets within the endplates along with the outer shell fully contain the supports. After the supports are in place, the expander instrument is removed, and the device remains in the expanded state.

Other objects and benefits of the invention will become apparent upon consideration of the following written description taken together with the accompanying figures.

DESCRIPTION OF THE EMBODIMENTS

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 1:
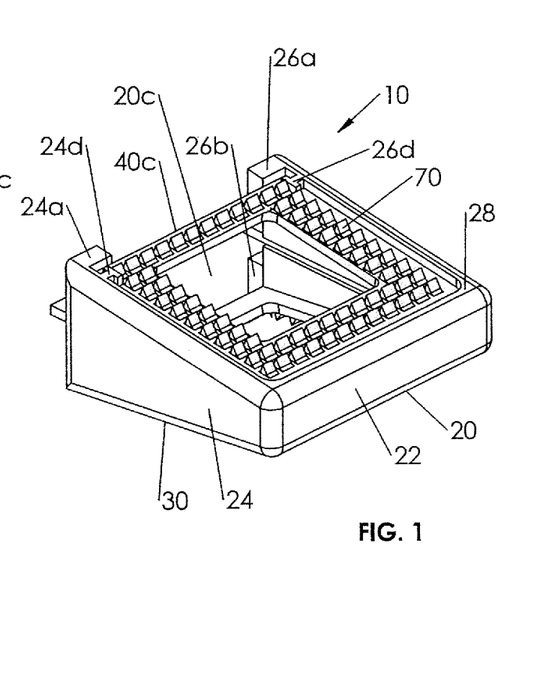
FIG. 1 is a top perspective view of an anterior lumbar interbody fusion device in accordance with one embodiment of the invention.
Figure 2:
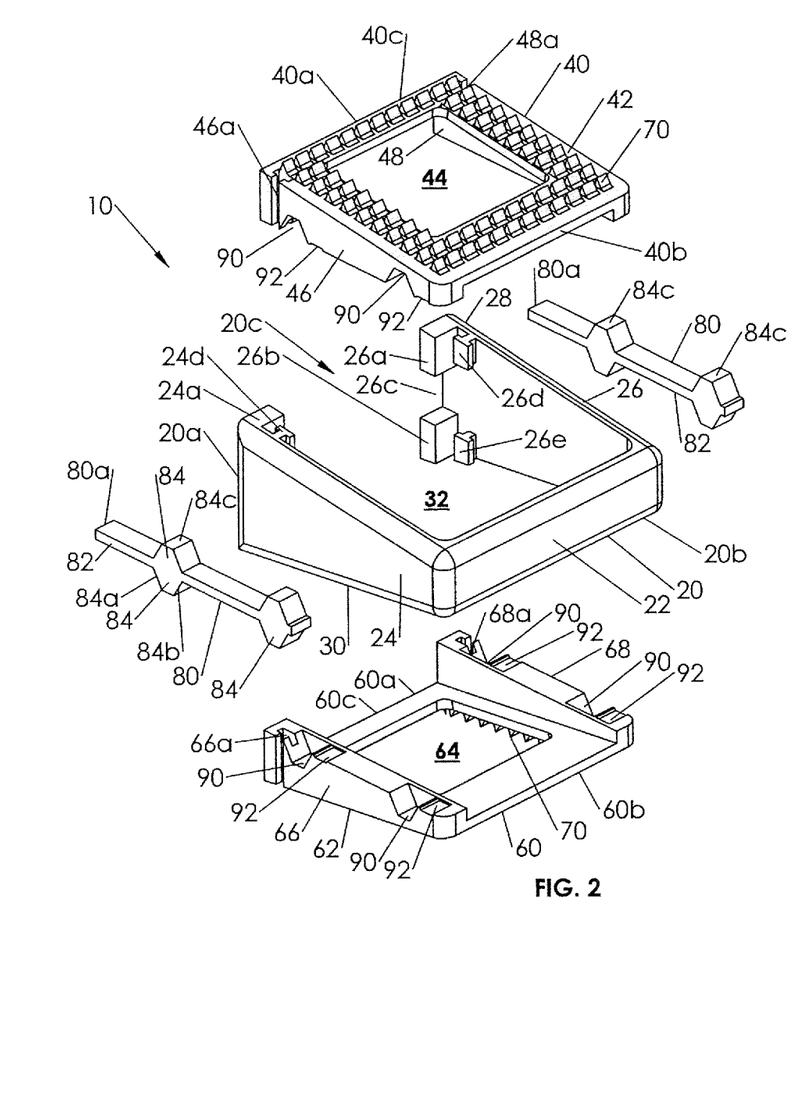
FIG. 2 is an exploded top perspective view of the anterior lumbar interbody fusion device of FIG. 1.
Figure 3:
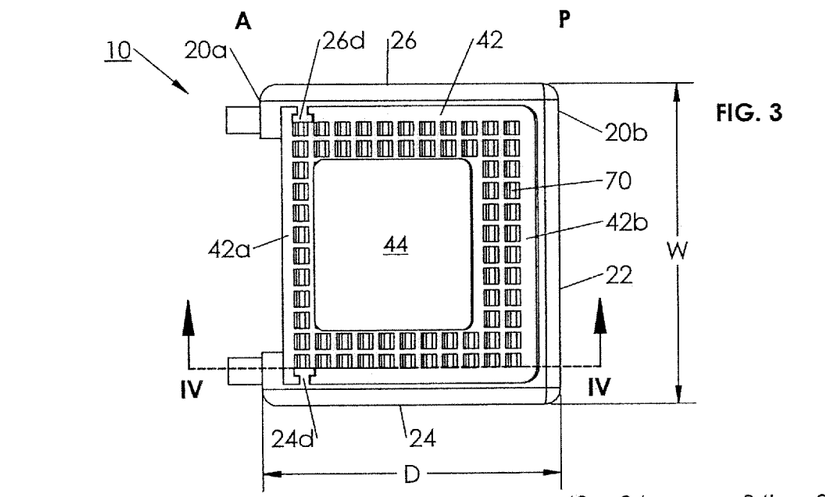
FIG. 3 is a top plan view of the anterior lumbar interbody fusion device of FIG. 1.

Described herein is an anterior lumbar interbody fusion device 10 for insertion into the intradiscal space between opposing vertebral bodies from the anterior approach. In particular, the described device 10 is suitable as a spinal fusion implant that is introduced at a lower profile and expanded along a height axis to a higher profile at the implantation site upon expansion by a secondary instrument. Turning now to FIGS. 1-3, details of device 10 are described. Device 10 in a particular arrangement comprises a shell 20, an upper endplate 40, a lower endplate 60 and a pair of opposing laterally spaced supports 80. Shell 20 has an anterior end 20a and a posterior end 20b defining an A-P direction as best seen in FIG. 3. Shell 20 further includes a posterior end wall 22, a pair of opposing sidewalls 24 and 26 defining a lateral direction, and a top surface 28 and a bottom surface 30 defining a height direction therebetween. Shell 20 has an open chamber 32 between posterior end wall 22 and opposing sidewalls 24 and 26, anterior end 20a of shell 20 having an open face 20c communicating with chamber 32. Shell 20 is formed as a wedge tapering downwardly from the anterior end 20a to the posterior end 20b.

As shown in FIG. 2, each sidewall 24 and 26 of shell 20 includes at the anterior end 20a a pair of retainer elements 24a and 24b (not shown) and 26a and 26b respectively, each of which projects partially laterally into open face 20c. Retainer elements 26a, 26b are spaced in the height direction by a spacing 26c having a dimension to allow introduction of a support 80 into shell 20 along sidewall 26, as will be described. Similarly, retainer elements 24a, 24b are spaced in the height direction by a spacing 24c (not shown) having a dimension to likewise allow introduction of a support 80 into shell 20 along sidewall 24. A pair of rails 26d and 26e are included on sidewall 26 respectively adjacent retainer elements 26a and 26b, rails 26d, 26e being configured to mate with tracks formed in upper endplate 40 and lower endplate 60 in a manner to guide movement of upper endplate 40 and lower endplate 60, as will be described. Rails 26d, 26e may be formed in a dovetail shape or other suitable configuration. Similarly, a pair of rails 24d and 24e (not shown) are included on sidewall 24 respectively adjacent retainer elements 24a and 24b, rails 24d, 24e being configured to likewise mate with tracks formed in upper endplate 40 and lower endplate 60 in a manner to guide movement of upper endplate 40 and lower endplate 60.

Referring still to FIG. 2, details of the upper endplate 40 and lower endplate 60 are described. In a particular arrangement of the ALIF device 10, upper endplate 40 and lower endplate 60 are structurally substantially identical, the upper and lower designator being associated with the orientation of each endplate in the device 10. As such, common features other than orientation will have common reference numerals. Focusing initially on lower endplate 60, it has an anterior end 60a, a posterior end 60b, and a lower surface 62 having a fully bounded lower opening 64 extending therethrough in communication with shell chamber 32 in assembly. Lower endplate 60 has a pair of opposing laterally spaced sidewalls 66 and 68 projecting upwardly from lower surface 62. In a particular arrangement, each sidewall 66, 68 has two deep first pockets 90 and two adjacent shallow second pockets 92 extending therein in the A-P direction. The details of deep pockets 90 and shallow pockets 92 will be described below. Sidewalls 66, 68 of lower endplate 60 respectively include adjacent anterior end 60a a track 66a and a track 68a. Tracks 66a and 68a are sized and configured to cooperatively receive rails 24e and 26e, respectively, upon assembly of lower plate 60 into shell 20 from the bottom surface 30.

Upper endplate 40 has an anterior end 40a, a posterior end 40b, and an upper surface 42 having a fully bounded upper opening 44 extending therethrough in communication with shell chamber 32 in assembly. Upper endplate 40 has a pair of opposing laterally spaced sidewalls 46 and 48 projecting downwardly from upper surface 42. In the particular arrangement being described, each sidewall 46, 48 has two deep first pockets 90 and two adjacent shallow second pockets 92 extending therein in the A-P direction. Deep pockets 90 and shallow pockets 92 of upper endplate 40 are in substantial alignment with respective deep pockets 90 and shallow pockets 92 of lower endplate 60 in assembly of device 10. Sidewalls 46, 48 of upper endplate 40 respectively include adjacent anterior end 40a a track 46a and a track 48a. Tracks 46a and 48a are sized and configured to cooperatively receive rails 24d and 26d, respectively, upon assembly of upper plate 40 into shell 20 from the top surface 28.

Figure 4A:
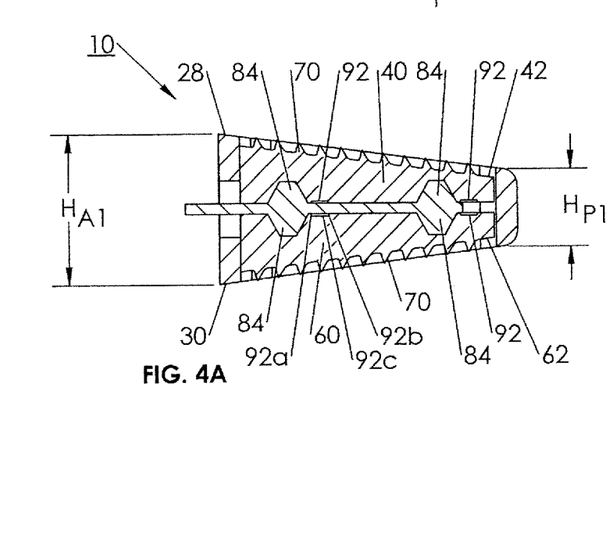
FIG. 4A is a cross-sectional view of the anterior lumbar interbody fusion device as seen along viewing lines IV-IV of FIG. 3 with the device being in an unexpanded position.
Figure 4B:
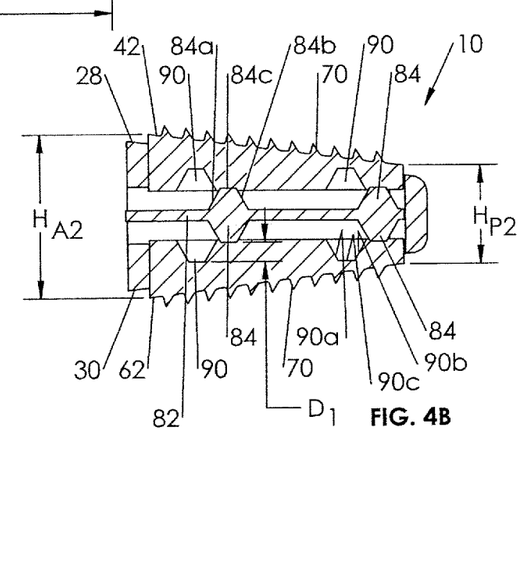
FIG. 4B is a cross-sectional view of the anterior lumbar interbody fusion device as seen along viewing lines IV-IV of FIG. 3 with device being in an expanded position.

Referring still to FIG. 2 and now also to FIGS. 4A and 4B, details of pockets 90 and 92 are described. Each deep pocket 90 of both upper endplate 40 and lower endplate 60 are substantially identical. Each deep pocket 90 in a particular arrangement is generally trapezoidal in shape, having a pair of opposing inclined surfaces 90a and 90b terminating in a support surface 90c, as shown in FIG. 4B. Each shallow pocket 92 in this particular arrangement is generally trapezoidal in shape, having a pair of opposing inclined surfaces 92a and 92b terminating in a support surface 92c, as shown in FIG. 4A. Pockets 90 and 92 are formed by cutting into the respective sidewalls of upper endplate 40 and lower endplate 60 from the exterior but not fully through the sidewalls, leaving a portion of the sidewalls intact as seen in FIG. 2, thereby providing a retention barrier to minimize or prevent supports 80 from slipping out from pockets 90, 92. In assembly of device 10, each of pockets 90, 92 is further bounded by an inner surface of the sidewalls 24, 26 of shell 20. The difference, $D_1$ between the depth of deep pocket 90 and shallow pocket 92 as illustrated in FIG. 4B determines the distance that the upper endplate 40 and the lower endplate each respectively moves in the height direction as device 10 is expanded, as will be described.

Referring again to FIGS. 2, 4A and 4B, details of supports 80 are described. As each of supports 80 is substantially identical, only one support 80 will be described. Support 80 comprises an elongate body 82 including at least two bosses 84 projecting upwardly and two bosses 84 projecting oppositely downwardly in the height direction. Each boss 84 in this particular arrangement is generally trapezoidal in shape, having a pair of opposing inclined surfaces 84a and 84b terminating in an engagement surface 84c, as shown in FIGS. 2 and 4B. The height of each boss 84 in this particular arrangement is approximately the same and is also approximately equal to or slightly greater than the distance $D_1$. The angles of inclination of inclined surfaces 84a and 84b are commensurate particularly with the angles of inclination inclined surfaces 90a and 90b of deep pocket 90. Each support 80 has an anterior surface 80a to facilitate movement of supports 80 between upper and lower endplates 40 and 60, as will be described. In some arrangements, supports 80 may be formed as a one-piece component with one of the upper endplate 40 or lower endplate 60 or with both upper endplate 40 and lower endplate 60, and be movably attached thereto by a deformable tether or the like.

Upper endplate 40 and lower endplate 60 also each preferably include bone fixation elements 70 projecting respectively from upper surface 42 and lower surface 62, as shown in FIGS. 1-3. These fixation elements 70 may function to assist in holding the device 10 in position after implantation, as will be described. In a particular arrangement, fixations elements are individual teeth each having a relatively sharp tip at the apex to penetrate a vertebral body endplate on either side of the intravertebral disc space in a manner to anchor device 10 within the disc space. Other forms of fixation elements 70, e.g. fins, spikes, hooks, etc., may be substituted as desired.

Referring now to FIGS. 3, 4A and 4B, certain features of device 10 are described. Device 10 is shown in FIG. 4A in the assembled unexpanded position. In this unexpanded position, upper endplate 40 and lower endplate 60 are inserted into shell chamber 32 from the top and bottom respectively. Rails 24d and 26d on shell sidewalls 24 and 26 are received in tracks 46a and 48a of upper endplate 40. Similarly, rails 24e and 26e on shell sidewalls 24 and 26 are received in tracks 66a and 68a of lower endplate 60. Supports 80 are inserted into shell 20 through respective spacings 24c, 26c and between upper endplate 40 and lower endplate 60. In this unexpanded position, supports 80 are contained within shell 20 with support bosses 84 all residing in a first position in deep pockets 90 and with engagement surfaces 84c each being in contact with support surfaces 90c of the respective deep pockets 90 of upper endplate 40 and lower endplate 60. Upper endplate 40 in this unexpanded position, is fully contained and nested within shell 20 with the apices of teeth 70 or other fixation elements lying below upper surface 28 of shell 20. Similarly, endplate 60 in this unexpanded position, is fully contained and nested within shell 20 with the apices of teeth 70 or other fixation elements lying above lower surface 30 of shell 20. As such, device 10 has an unexpanded leading edge height $H_{P1}$ at the posterior end 20b and an unexpanded trailing edge height $H_{A1}$ at the anterior end 20a, as depicted in FIG. 4A. Unexpanded heights $H_{P1}$ and $H_{A1}$ are effectively determined by the fixed heights of shell 20 at the respective posterior end 20b and anterior end 20a. Shell height $H_{A1}$ at the anterior end 20a may be greater than or equal to shell height $H_{P1}$ at the posterior end 20b, depending upon the particular application.

Referring now to FIG. 4B, device 10 is shown in the expanded position with supports 80 having been moved posteriorly in the A-P direction, as will be described, from the first position to a second position wherein support bosses 84 all reside in shallow pockets 92 with engagement surfaces 84c each boss being in contact with support surfaces 92c of the respective shallow pockets 92 of upper endplate 40 and lower endplate 60. As will be described, a secondary instrument causes upper endplate 40 to telescopically move upwardly, guided by rails 24d, 26d and tracks 46a, 48a, a distance, $D_1$. Substantially simultaneously, secondary instrument also causes lower endplate 60 to telescopically move downwardly, guided by rails 24e, 26e and tracks 66a, 68a, a distance, $D_1$. As such, total expansion of device 10 in this arrangement is double the distance $D_1$. In this expanded position, at least fixation elements 70 of upper endplate 40 and lower endplate 60 are caused to extend outwardly beyond respective top surface 28 and bottom surface 30 of shell 20. In a more preferred expansion, upper surface 42 of upper endplate 40 and lower surface lower endplate 60 are caused to extend outwardly beyond respective top surface 28 and bottom surface 30 of shell 20, as depicted in FIG. 4B. In this preferred expansion, device 10 has an expanded height $H_{P2}$ at the posterior end 20b and an expanded height $H_{A2}$ at the anterior end 20a, the expanded heights being measured between the upper surface 42 of upper endplate 40 and the lower surface 62 of lower endplate 60. It should be appreciated that disposition of bosses 84 in shallow pockets 92 will tend to keep supports 80 in place when a compressive load is placed on the endplates 40 and 60 by opposing vertebral bodies. In some alternate arrangements, supports 80 may be locked in place via flexible latches and may not require a compressive load to remain locked.

It should be understood that where the distance $D_1$ between each pair of deep pockets 90 and shallow pockets 92 is substantially the same and the heights of bosses 84 are likewise substantially the same, the rate of expansion of device 10 at the anterior end 20a and posterior end 20b will be substantially the same. In a situation where a greater amount of lordotic expansion is desired, device 10 may be expanded to create a greater amount of expansion at the anterior end 20a than at the posterior end 20b. Such an expansion may be effected by forming $D_1$ between pockets 90 and 92 adjacent anterior end 20a to be greater than $D_1$ between pockets 90 and 92 adjacent posterior end 20b, with a commensurate change in the configurations of bosses 84 and pockets 90 and 92.

Referring again also to FIG. 3, device 10 may have a width W and a depth D defining the footprint of device 10. The width W is defined as the maximum lateral distance between the outer surfaces of shell sidewalls 24 and 26 and the depth D is defined as the maximum distance between the anterior and posterior ends 20a and 20b of shell 20. In a particular arrangement, the maximum expanded height $H_{A2}$ at the anterior end 20a of device 10 is less than the maximum width W. Further, in a particular arrangement and depending upon the footprint, opening 44 through upper surface 42 which communicates with shell chamber 32 in assembly of device 10 may comprise an area in the range of about 25-60% of the area of upper surface 42. Similarly, opening 64 through lower surface 62 which also communicates with shell chamber 32 in assembly of device 10 may comprise an area in the range of about 25-60% of the area of lower surface 62. Such an opening to surface area ratio has been found to provide a sufficiently large enough area so as to maximize contact between graft material introduced into chamber 32 through open face 20c and the endplates of opposing vertebral bodies while providing sufficient structural surface area to minimize subsidence. In this regard, as illustrated in FIG. 3 a portion 42b of the surface area of outer surface 42 of upper endplate 40 adjacent posterior end 20b is greater than a portion 42a of the surface area of outer surface 42 adjacent anterior end 20a. Anterior and posterior portions of lower surface area 62 of lower endplate 60 may be similarly formed. It should be appreciated, however, that the ratio of the upper and lower openings to the respective surface areas of device 10 may be varied depending upon different circumstances and applications.

Device 10 may comprise a suitable biocompatible material. For example, shell 20, upper endplate 40, lower endplate 60 and supports 80 may be formed of pure titanium, although other materials such as, tantalum, cobalt-chromium alloys, titanium alloys (e.g., nickel titanium alloys and tungsten titanium alloys), and stainless steel alloys may also be used. Each of shell 20, upper and lower endplates 40 and 60, and supports 80, may in some methods of manufacture, be machined or formed by a 3-D printing technique. In some applications, suitable polymeric materials may be used, including members of the polyaryletherketone (PAEK) family, e.g., polyetheretherketone (PEEK), carbon-reinforced PEEK, polyetherketoneketone (PEKK); polysulfone; polyetherimide; polyimide; ultra-high molecular weight polyethylene (UHMWPE); or cross-linked UHMWPE. In addition, upper and lower surfaces 42, 62 of respective upper and lower endplates 40, 60 may have a surface texture that allows for boney ingrowth. Such, surface texture may be in the form of a spray or coating of titanium or other bone growth promoting substances.

Devices 10 as described herein, may be provided in various sizes and dimensions to accommodate different anatomical conditions and surgical applications. For example, devices 10 may having a width W in the range of 25 to 50 mm and a depth D in the range of 20 to 40 mm. Devices 10 may have an unexpanded posterior leading end height $H_{P1}$ in the range of 3 to 17 mm and an unexpanded anterior trailing end height $H_{A1}$ in the range of 8 to 19 mm. Devices 10 may have an expanded posterior end height $H_{P2}$ in the range of 5 to 15 mm and an expanded anterior end height $H_{A2}$ in the range of 9 to 19 mm. Different angles of lordosis may be provided by varying the amount of expansion between the anterior and posterior ends of the devices 10. Alternatively, different lordotic angles may be achieved by forming the shell 20 and endplates 40, 60 to have different fixed angles. It should be appreciated that the examples set forth herein are illustrative and that other sizes and dimensions of devices 10 may also be provided depending upon the patient needs and surgical requirements.

Kits containing a plurality of differently sized devices 10 discussed above may be provided where the devices 10 are selected to include a variety of expanded heights with appropriately sized and configured supports 80, or selected to have differing collapsed heights, or differing widths or depths, or are selected to include differing lordotic angles between the posterior and anterior ends. Each of these kits may further include instrumentation to introduce the devices into a chosen site in the intradiscal space between opposing vertebral bodies.

Figures 5, 6:
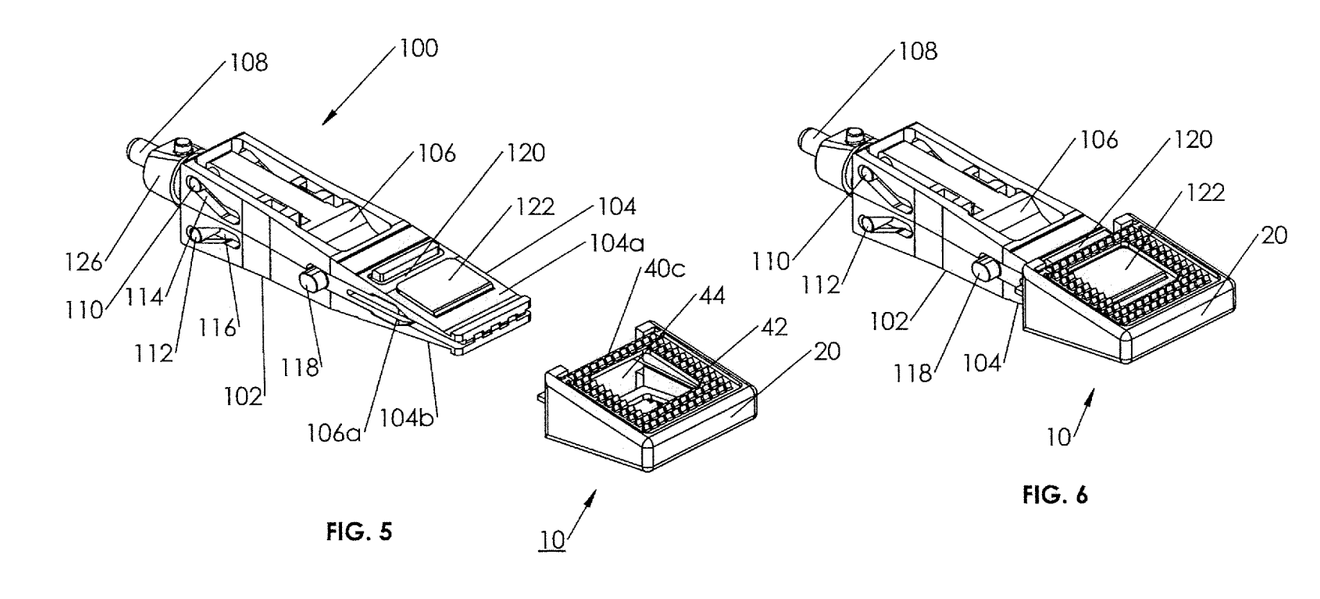
FIG. 5 is an exploded top perspective view of the unexpanded anterior lumbar interbody fusion device of FIG. 1 and a tool portion of an instrument for use in inserting and expanding the collapsed device.
FIG. 6 is a top perspective view of the device and instrument of FIG. 5 with the tool portion attached to the anterior lumbar interbody fusion device before expansion.

Turning now to FIG. 5, one arrangement of secondary instrumentation 100 for use in inserting device 10 into the intradiscal space and expanding device 10 therein is described. Such instrumentation 100 may include a modular tool portion 102 including an expandable tip 104 specifically configured for receipt into interior open face 20c of a device 10. Tip 104 includes a pair of plates, namely upper plate 104a and lower plate 104b that are movably separated by an axially translatable wedge 106. Wedge 106 is coupled to an axially movable shaft 108 that in turn is coupled to an actuator (not shown) that may drive shaft 108 by means of a rotatable screw mechanism or any other suitable mechanism. Wedge 106 has a proximal extent 106a that is sized and configured to extend between plates 104a and 104b and upon axial movement of wedge 106 to engage and separate plates 104a and 104b apart from each other. A pair of pins 110 and 112 is coupled to wedge 106 adjacent the distal end, pins 110, 112 being sized and configured to ride within slots 114 and 116 of respective plates 104a, 104b as wedge is translated axially distally in a manner to maintain upper plate 104a and lower plate 104b together during separation. Coupled to wedge 106 for axial movement therewith is a pusher 118 in the form of a shaft that extends transversely across tool portion 102. The advancement mechanism of tool portion 102 is configured such that wedge extent 106a will advance initially between upper plate 104a and lower plate 104b to move the upper endplate 40 and lower endplate 60 apart before pusher 118 is advanced axially distally.

Included on the distal end of upper plate 104a is a trailing ledge 120 and a pad 122. Pad 122 is spaced from both trailing ledge 122 a predetermined distance to accommodate differently sized devices 10. Pad 122 is particularly sized and spaced to fit within opening 44 through upper endplate 42. Trailing ledge 120 is spaced proximally from pad 122 a predetermined distance such that when pad 122 is situated in endplate opening 44, trailing ledge 120 engages surface 40c at the anterior end 40a of upper endplate 40. Although not shown, lower plate 104b is formed to have a pad, a trailing ledge and a leading edge similar to upper plate 104a for attachment to lower endplate 60 in the same manner that upper plate 104a is attached to upper endplate 40. Tool portion 102 may be suitably separably connected to the actuator by a quick release coupler 126. As such, a variety of tool portions 102 may be provided in a kit, each of which includes an expandable tip 104 having particularly configured and dimensioned pads, trailing ledges and leading edges for mating to the size of a selected device 10. A selected tool portion 102 is suitably attached to a selected device 10 by insertion of expandable tip 104 into chamber 32 of shell 20 through open face 20c. Plates 104a and 104b contact respective interior surfaces of upper endplate 40 and lower endplate 60 upon attachment. As wedge 106 is driven distally upon axial movement of shaft 108, plates 104a and 104b are moved apart thereby moving apart upper endplate 40 and lower endplate 60 along the height axis to expand device 10, as described hereinabove.

Figure 7:
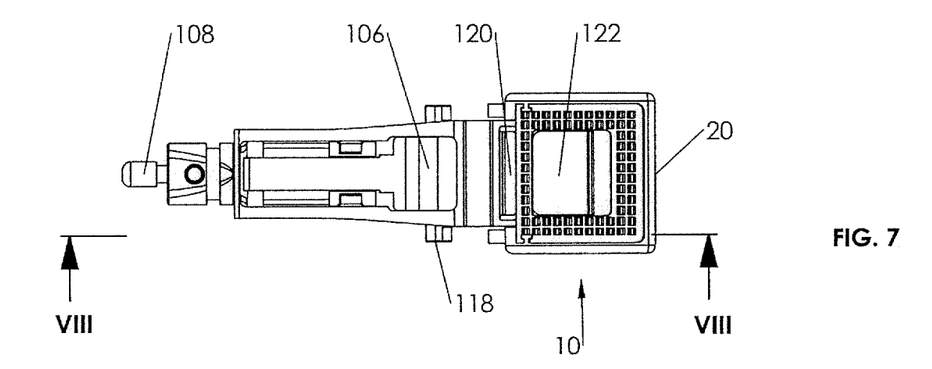
FIG. 7 is a top plan view of the attached anterior lumbar interbody fusion device and tool portion of FIG. 6.
Figure 8:
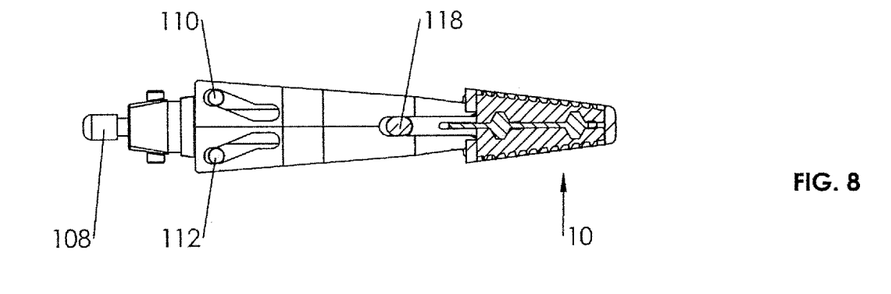
FIG. 8 is a cross-sectional view of the attached anterior lumbar interbody fusion device and tool portion as seen along viewing lines VIII-VIII of FIG. 7.

Having described the structure and function of device 10 herein, the method of using device 10 in an anterior lumbar interbody fusion is now described. An incision is made through the patient's abdomen and the surrounding muscles and abdominal contents are retracted to the side to form an open surgical access corridor. The affected disc is removed to provide a proper space between opposing vertebral bodies. The surgeon may determine the appropriate size of a device 10 for insertion by using a suitable trialing device and fluoroscopy. Once the appropriate size is determined, a desired device 10 is selected from the kit as described above and suitably attached to a selected tool tip 104, as shown in FIG. 6-8. As attached, device 10 is in the unexpanded position as shown in FIG. 4A. The device 10 is inserted into the disc space by tool portion 102 through manipulation of the actuator by the surgeon. As the fixation elements 70 in this unexpanded position are fully contained within shell 20, device 10 may atraumatically enter the disc space for proper positioning.

Figure 9:
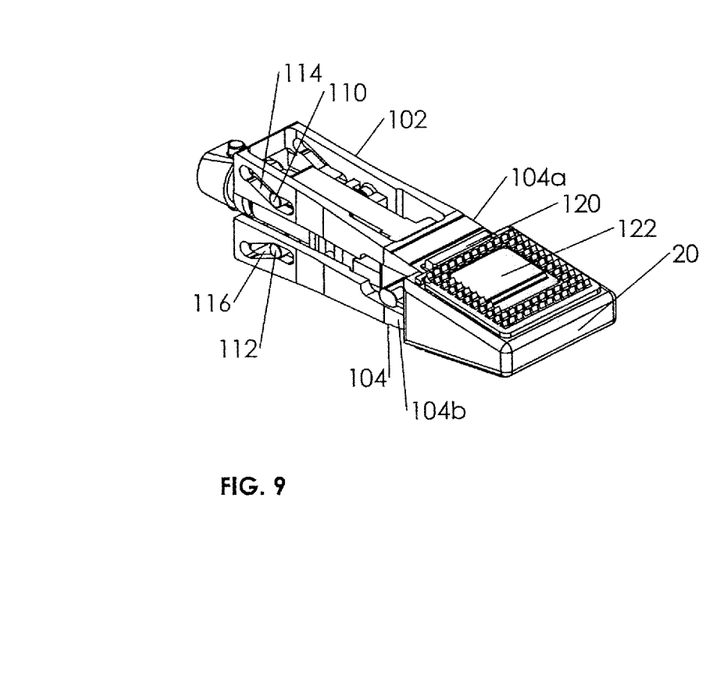
FIGS. 9-11 are further views of FIGS. 6-8 showing the step of distracting the anterior lumbar interbody fusion device with the tool portion.
Figure 10:
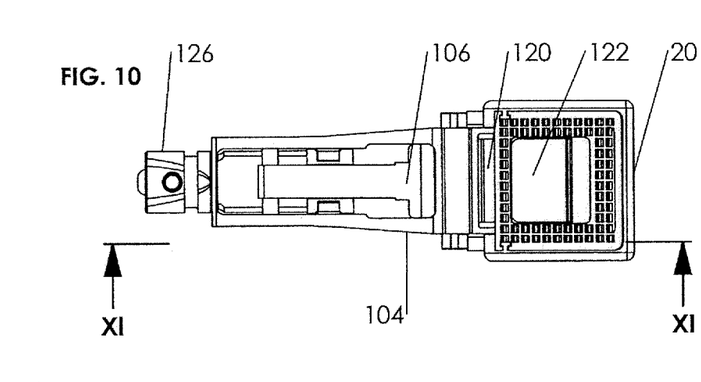
Figure 11:
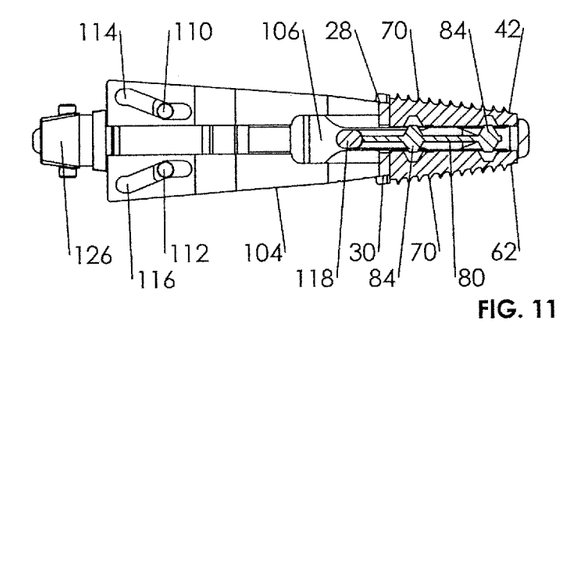
Figure 12:
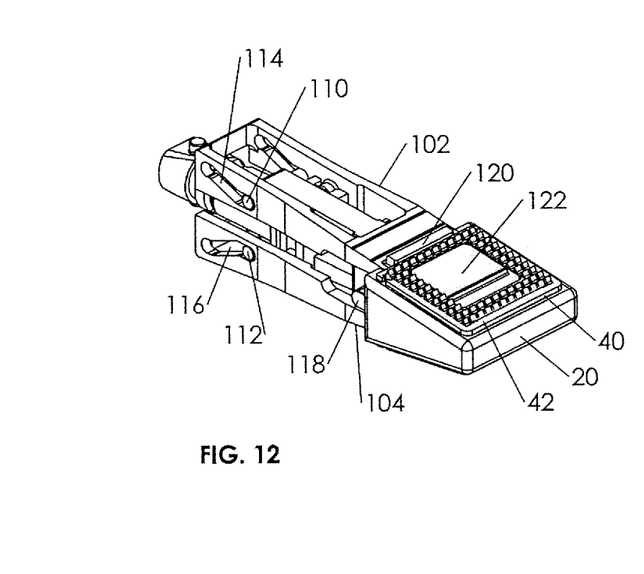
FIGS. 12-14 are further views of FIGS. 9-11 showing the step of introducing supports into the expanded anterior lumbar interbody fusion device with the tool portion.
Figure 13:
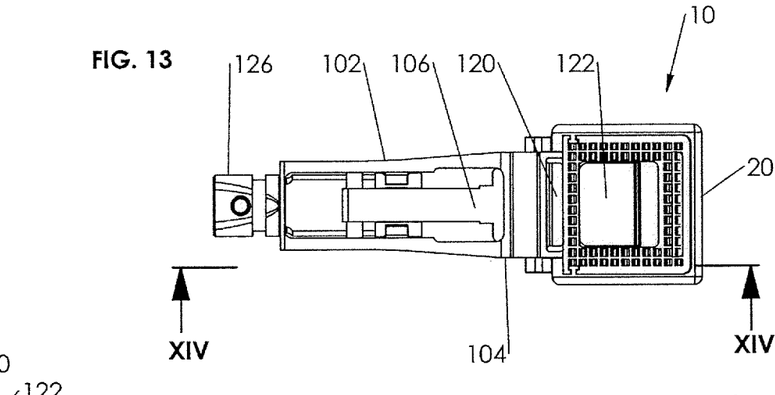
Figure 14:
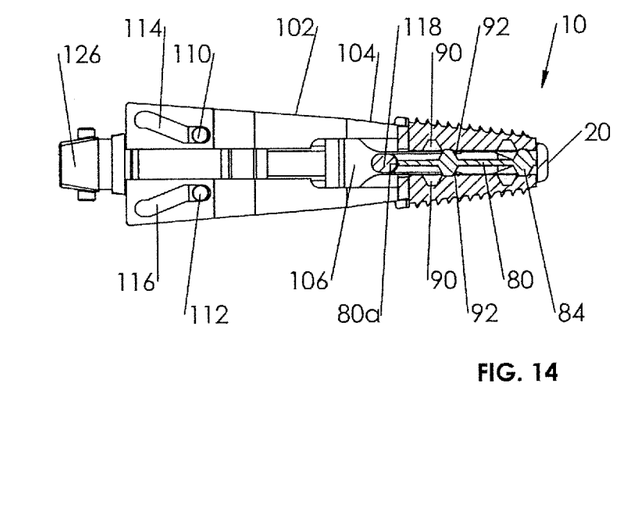

Once suitably introduced into the disc space, device 10 is expanded by axial movement of wedge 106 distally as described herein to separate plates 104a and 104b apart from each other, as shown in FIGS. 9-11. In the particular arrangement described above wherein upper surface 42 and lower surface 62 of respective upper and lower endplates 40 and 60 are moved respectively above and below top and bottom surfaces 28 and 30 of shell 20, the disc space will be distracted by the respective upper and lower surfaces 42 and 62 upon expansion of device 10. Further, upon expansion, device 10 provides for instantaneous fixation to the opposing vertebral bodies by penetration of the vertebral body endplates by fixation elements 70, without use of a secondary fixation member.

After device 10 is expanded, continued axial movement of shaft 108 will then distally move pusher 118 into engagement with anterior end 80a of each support 80 causing supports 80 to move distally from the first position of FIG. 4A to the second position as shown in FIGS. 4B and 12-14. During such movement, inclined surfaces 84b of bosses 84 will slide against opposing inclined surfaces 90b of deep pockets 90, forcing opposing upper and lower endplates 40 and 60 apart as each support moves forward. Bosses 84 move into shallow recesses 92, as depicted in FIGS. 4B and. 14, as full expansion is reached.

Figure 15:
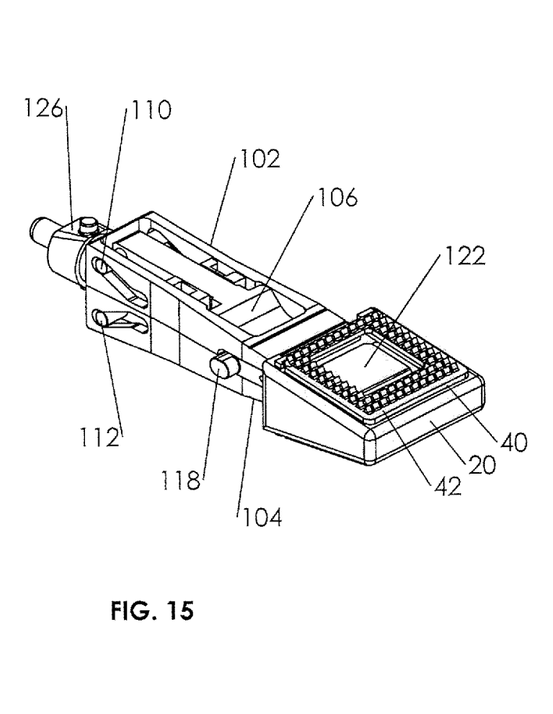
FIGS. 15-17 are further views of FIGS. 12-14 showing the step of collapsing the tool portion prior to removal of the tool portion from the expanded anterior lumbar interbody fusion device.
Figures 16, 17:
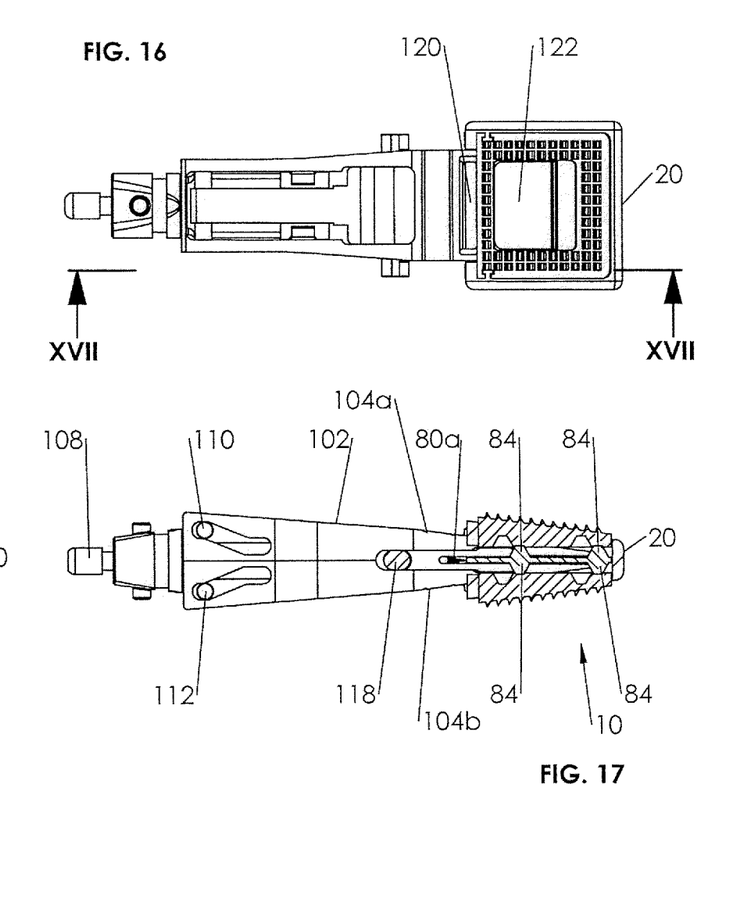

Once device 10 is properly expanded, tool portion 102 is actuated to move wedge 106 axially in the reverse direction. Movement of wedge 106 proximally causes pusher 118 to separate from anterior surface 80a of each support 80 and upper plate 104a and lower plate 104b to collapse toward each other as shown in FIGS. 15-17. At this point in the procedure, the instrumentation 100 may be removed from the surgical site. All or a portion of the chamber 32 of device 10 as well as the disc space surrounding expanded device 10 may be filled in situ through open face 20c with a suitable bone graft material containing bone growth promoting substances. Other suitable osteogenic materials or therapeutic compositions may also be used. If desired, open face 20c may be covered with a suitable cap or plate in a manner to prevent graft material from escaping device 10.

It should now be appreciated that the expandable anterior lumbar interbody fusion device 10 described herein may be inserted into a smaller intradiscal disc space than a non-expandable fusion device, thereby minimizing damage to bony structure that may be associated with heavy impaction. Additionally, expansion of device 10 provides indirect decompression of adjacent neural elements while maintaining appropriate lordosis of the patient's spine. The expandable wedge configuration of upper endplate 40 and lower endplate 60 allows for deformity correction of the spine as well as sagittal balance restoration while providing both posterior and anterior disc space distraction. Furthermore, the open architecture of device 10, particularly of the upper and lower openings 44 and 64 through upper endplate and lower endplate respectively allows for preparation of vertebral endplates through the open face 20c of device 10 after insertion, which may potentially reduce subsidence. Such openness of device 10 also allows for packing of more bone graft material.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

The supports have features for locking in place when a compressive load is placed on the endplates. In some alternate embodiments, supports may be locked in place via flexible latches and may not require a compressive load to remain locked.

What is claimed is:

1. An expandable anterior lumbar interbody fusion device, comprising:
a shell having an anterior end and a posterior end defining an anterior-posterior direction, a posterior end wall, a pair of spaced opposing sidewalls defining a lateral direction, and a top surface and a bottom surface defining a height direction, said shell having a chamber between said posterior end wall and said opposing sidewalls, said anterior end having an open face communicating with said chamber, said anterior end having a height in the height direction greater than or equal to a height at said posterior end;
an upper endplate having an anterior end, a posterior end and an upper surface having a fully bounded upper opening extending therethrough in communication with said chamber, said upper endplate having a pair of opposing laterally spaced sidewalls projecting downwardly from said upper surface, said upper endplate being fully contained within said shell and supported by said shell for telescopic movement in the height direction from an unexpanded position to an expanded position;
a lower endplate having an anterior end, a posterior end and a lower surface having a fully bounded lower opening extending therethrough in communication with said chamber, said lower endplate having a pair of opposing laterally spaced sidewalls projecting upwardly from said lower surface in substantial alignment with said sidewalls of said upper endplate, said lower endplate being fully contained within said shell and supported by said shell for telescopic movement in the height direction from an unexpanded position to an expanded position;
a pair of laterally spaced supports movably disposed between said respective upper endplate sidewalls and said lower endplate sidewalls, said supports supporting said upper endplate and said lower endplate in at least said expanded position.

2. The device of claim 1, wherein said upper endplate comprises fixation elements projecting from said upper surface and wherein said lower endplate comprises fixation elements projecting from said lower surface, said fixation elements of both said upper endplate and said lower endplate being fully contained within said shell with said device in said unexpanded position.

3. The device of claim 2, wherein said fixation elements on said upper endplate project outwardly above said top surface of said shell with said device in said expanded position, and wherein said fixation elements on said lower endplate project outwardly below said bottom surface of said shell with said device in said expanded position.

4. The device of claim 3, wherein said fixation elements on said upper endplate and said lower endplate comprises a plurality of teeth.

5. The device of claim 3, wherein said upper surface of said upper endplate projects outwardly above said top surface of said shell with said device in said expanded position, and wherein said lower surface of said lower endplate projects outwardly below said bottom surface of said shell with said device in said expanded position.

6. The device of claim 5, wherein said device expands at said anterior end and said posterior end at a same rate.

7. The device of claim 5, wherein said device expands at said anterior end at a rate greater than expansion at the posterior end.

8. The device of claim 5, wherein said upper opening through said upper endplate has an area in a range of 25-60% of the surface area of said outer surface of said upper endplate.

9. The device of claim 8, wherein said lower opening through said lower endplate has an area in a range of 25-60% of the surface area of said outer surface of said lower endplate.

10. The device of claim 1, wherein a portion of a surface area of said outer surface of said upper endplate adjacent said posterior end is greater than a portion of a surface area of said outer surface of said upper endplate adjacent said anterior end.

11. The device of claim 10, wherein a portion of a surface area of said outer surface of said lower endplate adjacent said posterior end is greater than a portion of a surface area of said outer surface of said lower endplate adjacent said anterior end.

12. The device of claim 1, wherein said shell has a width defined by a maximum distance between an outer surface of said opposing sidewalls, and wherein said device has a maximum expanded height less than said maximum distance.

13. The device of claim 1, wherein said supports are contained within said shell and are movable between and in engagement with respective opposing sidewalls of said upper endplate and said lower endplate from a first position in which said device is unexpanded to a second position in which said device is expanded.

14. The device of claim 13, wherein each of said supports includes at least two bosses projecting upwardly and two bosses projecting oppositely downwardly in the height direction, said bosses engaging said respective sidewalls of said upper endplate and said lower endplate and maintaining expansion of said device upon movement of said supports from the first position to the second position.

15. An expandable anterior lumbar interbody fusion device, comprising:
a shell having an anterior end and a posterior end defining an anterior-posterior direction, a posterior end wall, a pair of spaced opposing sidewalls defining a lateral direction, and a top surface and a bottom surface defining a height direction, said shell having a chamber between said posterior end wall and said opposing sidewalls, said anterior end having an open face communicating with said chamber, said anterior end having a height in the height direction greater than or equal to a height at said posterior end;
an upper endplate having an anterior end, a posterior end and an upper surface having a fully bounded upper opening extending therethrough in communication with said chamber, said upper endplate having a pair of opposing laterally spaced sidewalls projecting downwardly from said upper surface, each of said sidewalls having two deep first pockets and two shallow second pockets extending therein in the A-P direction, said upper endplate being fully contained within said shell and supported by said shell for telescopic movement in the height direction from an unexpanded position to an expanded position;
a lower endplate having an anterior end, a posterior end and a lower surface having a fully bounded lower opening extending therethrough in communication with said chamber, said lower endplate having a pair of opposing laterally spaced sidewalls projecting upwardly from said lower surface in substantial alignment with said sidewalls of said upper endplate, each of said sidewalls having two deep first pockets and two shallow second pockets extending therein in the A-P direction in substantial alignment with said respective first and second pockets of said upper endplate, said lower endplate being fully contained within said shell and supported by said shell for telescopic movement in the height direction from an unexpanded position to an expanded position;
a pair of laterally spaced supports contained within said shell and movable respectively between said upper endplate and said lower endplate, each of said supports including a first pair of bosses projecting upwardly and a second pair of bosses projecting oppositely downwardly in the height direction, said projecting bosses being disposed in said respective deep first pockets with said device in said unexpanded position and disposed in said respective shallow second pockets with said device and said expanded position.

16. The device of claim 15, wherein each of said pockets is defined in part by an inner surface of the sidewalls of said shell.

17. The device of claim 16, wherein each of said pockets is defined in further part by a portion of respective sidewalls of said upper endplate and said lower endplate.

18. The device of claim 15, wherein said upper endplate comprises fixation elements projecting from said upper surface and wherein said lower endplate comprises fixation elements projecting from said lower surface, said fixation elements of both said upper endplate and said lower endplate being fully contained within said shell with said device in said unexpanded position.

19. The device of claim 18, wherein said fixation elements on said upper endplate project outwardly above said top surface of said shell with said device in said expanded position, and wherein said fixation elements on said lower endplate project outwardly below said bottom surface of said shell with said device in said expanded position.

20. The device of claim 19, wherein said upper surface of said upper endplate projects outwardly above said top surface of said shell with said device in said expanded position, and wherein said lower surface of said lower endplate projects outwardly below said bottom surface of said shell with said device in said expanded position.

21. A kit of parts for use in anterior lumbar interbody fusion, comprising:
a plurality of differently sized expandable anterior lumbar interbody fusion devices, each device including a shell having a posterior end, an anterior end and an interior chamber, each device comprising an upper endplate including an upper surface having a fully bounded opening therethrough and a lower endplate including a lower surface having an opening therethrough, a distance between said upper surface and said lower surface of each device defining a height direction, said upper endplate and said lower endplate being movable relative to said shell in said height direction to expand said device; and
an instrument adapted to attach to a selected one of said devices, insert said selected device into a disc space between opposing vertebral bodies of a spine and expand said selected device therein, said instrument comprising a set of different modular tool portions each having an expandable tip adapted to be selectively attached to different ones of said selected devices.

22. The kit of parts of claim 21, wherein each of said plurality of devices is expandable a same distance at the posterior end and said anterior end.

23. The kit of parts of claim 21, wherein each of said plurality of devices expands greater at said anterior end than at said posterior end.

24. The kit of parts of claim 21, wherein said upper endplate of each of said plurality of devices comprises fixation elements projecting from said upper surface and wherein said lower endplate comprises fixation elements projecting from said lower surface, said fixation elements being adapted to extend outwardly beyond said shell in the height direction upon expansion.

25. The kit of parts of claim 21, wherein said expandable tip of each modular tool portion includes an upper plate and a lower plate, said upper plate and said lower plate adapted to engage an interior surface respectively of said upper endplate and said lower endplate of a selected device, said upper plate and said lower plate being adapted to move apart to thereby move apart said upper endplate and said lower endplate in the height axis to expand said selected device.

26. The kit of parts of claim 25, wherein said upper plate and said lower plate of each of said expandable tips comprises a pad adapted and configured to fit within respective openings through said upper endplate and said lower endplate.

27. The kit of parts of claim 26, wherein said upper plate and said lower plate of each of said expandable tips further comprises a ledge spaced from said pad a predetermined distance associated with a selected device, each ledge being adapted to respectively engage an anterior surface of said upper endplate and said lower endplate.

28. The kit of parts of claim 21, wherein each of said plurality of devices comprises a pair of supports adapted to be moved between said upper endplate and said lower endplate and to maintain each of said devices in at least said expanded position.

29. The kit of parts of claim 28, wherein said pair of supports of each of said plurality of devices is differently sized for maintaining the expanded position of each device at different heights in the height direction.

30. The kit of parts of claim 29, wherein said pair of supports of each of said plurality of devices is contained within each of said respective devices in the unexpanded position.

* * * * *